United States Patent [19]

McNeil et al.

[11] Patent Number: 5,571,141
[45] Date of Patent: Nov. 5, 1996

[54] DEVICE AND METHOD FOR CARDIAC ARRHYTHMIA THERAPY WITH FAILURE DETECTION AND BACKUP

[75] Inventors: Ken R. McNeil, Valencia, Calif.; Lee A. Cantrell, Freeport, Tex.; Balakrishnan Shankar, Santa Clarita, Calif.

[73] Assignee: Intermedics, Inc., Angleton, Tex.

[21] Appl. No.: 316,254

[22] Filed: Sep. 30, 1994

[51] Int. Cl.⁶ .................................................. A61N 1/39
[52] U.S. Cl. .................................................. 607/5
[58] Field of Search .................... 607/5, 27, 29, 607/63, 4

[56] References Cited

U.S. PATENT DOCUMENTS

| | | |
|---|---|---|
| 4,088,139 | 5/1978 | Auerbach . |
| 4,096,865 | 6/1978 | Auerbach . |
| 4,164,227 | 8/1979 | Auerbach . |
| 4,164,946 | 8/1979 | Langer . |
| 4,416,282 | 11/1983 | Saulson et al. ............................ 607/29 |
| 4,448,197 | 5/1984 | Nappholz et al. ........................ 607/29 |
| 4,532,934 | 8/1985 | Kelen ........................................ 607/27 |

*Primary Examiner*—William E. Kamm
*Assistant Examiner*—Scott M. Getzow
*Attorney, Agent, or Firm*—Wigman, Cohen, Leitner & Myers, P.C.

[57] ABSTRACT

An implantable automatic cardioverter/defibrillator device for a cardiac patient has a primary control mode for a defibrillation therapy delivery system. The primary control mode is responsive to detection of fibrillation of the patient's heart for causing the delivery of a preselected electrical waveform therapy to the heart. The device also has a secondary control mode which is enabled by detecting a predetermined failure mechanism that causes malfunctioning of the primary mode. The enabled secondary control mode uses at least some of the functional part of the primary mode in responding to fibrillation of the patient's heart to initiate generation of defibrillation therapy for application to the patient's heart.

12 Claims, 1 Drawing Sheet

DEVICE AND METHOD FOR CARDIAC ARRHYTHMIA THERAPY WITH FAILURE DETECTION AND BACKUP

BACKGROUND OF THE INVENTION

The present invention relates generally to medical devices for delivering cardiac arrhythmia therapy, and more particularly to an implantable device that provides a primary means for defibrillating a patient's heart and also provides a simple secondary means for defibrillation in the event of a failure of the primary means.

Pathologic ventricular tachycardia is characterized by rapid contractions of the heart's main pumping chambers, attributable to cardiovascular disorder. As a consequence of the rapid synchronous contractions, cardiac output is reduced because the ventricles are only partially filled with each heartbeat, resulting in delivery of a lowered supply of oxygenated blood to the extremities. If the ventricular tachycardia accelerates into ventricular fibrillation, the contractions of the individual cells of myocardial tissue become uncoordinated rather than synchronous with the result that cardiac output drops precipitously, and death will soon follow, absent prompt delivery of defibrillation therapy.

Typically, an antitachycardia pacemaker is implanted in the body of the afflicted cardiac patient and programmed to overstimulate the heart by delivering relatively low energy pulses at a constant rate or at varying rapid rates to suppress premature ventricular contractions. Cardioversion therapy involves delivery of electrical shocks of somewhat higher energy than the usual antitachy pulses to the heart to break the tachycardia. These therapies can lead to acceleration of a tachycardia into ventricular fibrillation in certain circumstances, so it is desirable that a defibrillating therapy be made available in the implanted device. To defibrillate the heart, one or more electrical shocks are delivered to the appropriate cardiac mass with sufficiently high energy level in an effort to halt the randomness and restore coordinated contractions of the cardiac tissue of the mass of cardiac tissue.

Multi-function automatic implantable devices may deliver a combination of therapies depending on the needs of the patient, particularly patients who are at high risk of ventricular fibrillation. Thus, it is usually proposed that automatic implantable defibrillators should be capable of performing not only defibrillation, but bradycardia and antitachycardia pacing, and cardioversion, as well. A conventional programmable pulse generator may be used for the pacing functions, with the addition of one or more relatively high capacity output storage capacitors and associated switching circuits for the charging and output functions required to produce high and relatively lower energy pulse shocks.

The appropriate therapy is to be delivered by the implanted device in response to sensing of physiologic functions or parameters of the cardiovascular system, sometimes in conjunction with other indicia of cardiac rate disorder, by means of one or more selectively positioned sensors. Typically, continuous monitoring of electrical signals indicative of the patient's cardiac activity is performed to verify that the therapy is having the desired effect, and, if it is not, to cause the delivery of additional therapy which may be more aggressive than that previously delivered, within the capability of the implanted device.

In general, while proposals have been made to provide implantable medical devices having the capability to perform a variety of different cardiac therapeutic functions, little or no attention has been given to the matter of potential device failure apart from the use of battery monitors, recommended periodic visits by the patient to the attending physician for device checks, and the like.

It is a principal object of the present invention to provide improved implantable medical devices in which device failure that would otherwise preclude defibrillation therapy is detected and corrected within the device itself, without need for surgical removal or replacement of the device.

SUMMARY OF THE INVENTION

The invention addresses the problem of a failure, other than the power source, that could render the device inoperative in the case of patient fibrillation. According to a presently preferred embodiment of the invention, an implantable defibrillator has means for detecting any of predetermined types of failure mechanisms of the primary control mode for defibrillation, and means responsive to detection of failure for thereupon enabling a secondary control mode of the device to assume control of the treatment of the sensed arrhythmia. If, after the secondary control mode is enabled the dysrhythmia is detected, to persist or recur, further defibrillation therapy is generated by the device.

The method of the invention includes continuously monitoring the patient's cardiac activity and/or other predetermined physiologic parameter indicative of heart rate, enabling the secondary control mode upon detection of a predetermined type of failure mechanism of the primary control mode, and shifting control of the delivery of therapy to the secondary control mode on the next detection of the arrhythmia.

The primary and secondary control modes may share certain common elements of the operating system of the device. Alternatively, the two modes may be completely distinct from one another structurally and functionally in their exercise of control over the operating system of the implanted device.

It is therefore another object of the invention to provide an implantable device for treating cardiac or cardiovascular disorders, such as atrial or ventricular tachycardia or fibrillation, in which the device includes means for performing redundant functions to provide backup capability for defibrillation in the event of certain types of failure of the device's operating system.

Yet another object of the invention is to provide dual control modes for the operating system of an implantable defibrillator to avoid catastrophic failure of the device if one control mode malfunctions.

An important aspect of the invention is the provision of the secondary control mode as a standby mode to assume control of generation and delivery of the proper therapy regimen from the failed primary mode, without the need for complex and expensive components or complete redundancy by mere duplication of the primary control mode elements. For example, in the case of a microcontroller-based device in which the microcontroller has considerable associated memory and which together operate as a control mode, it would add considerably to the device cost to duplicate the primary control mode system as a standby mode system.

Therefore, yet another important object of the invention is to provide an implantable cardiac therapeutic device with a standby mode to assure generation of the proper therapy despite a failure of the primary control system of the device, by means of a simple and inexpensive arrhythmia detection system.

BRIEF DESCRIPTION OF THE DRAWINGS

The above and other objects, aspects, features and attendant advantages of the invention will be recognized from the following detailed description of a preferred embodiment and method constituting the presently contemplated best mode of practicing the invention, in conjunction with the accompanying drawings, in which.

DESCRIPTION OF THE PREFERRED EMBODIMENT AND METHOD

The principles of the present invention are applicable to various implantable medical devices, but the most effective application resides in devices whose overall system control resides principally in a single element. An example is where the control element is a central processing unit (CPU) such as a semiconductor integrated circuit chip microprocessor with associated on-chip or off-chip memory, such as is used in current versions of an automatic implantable cardioverter/defibrillator (ICD).

Figure 1:
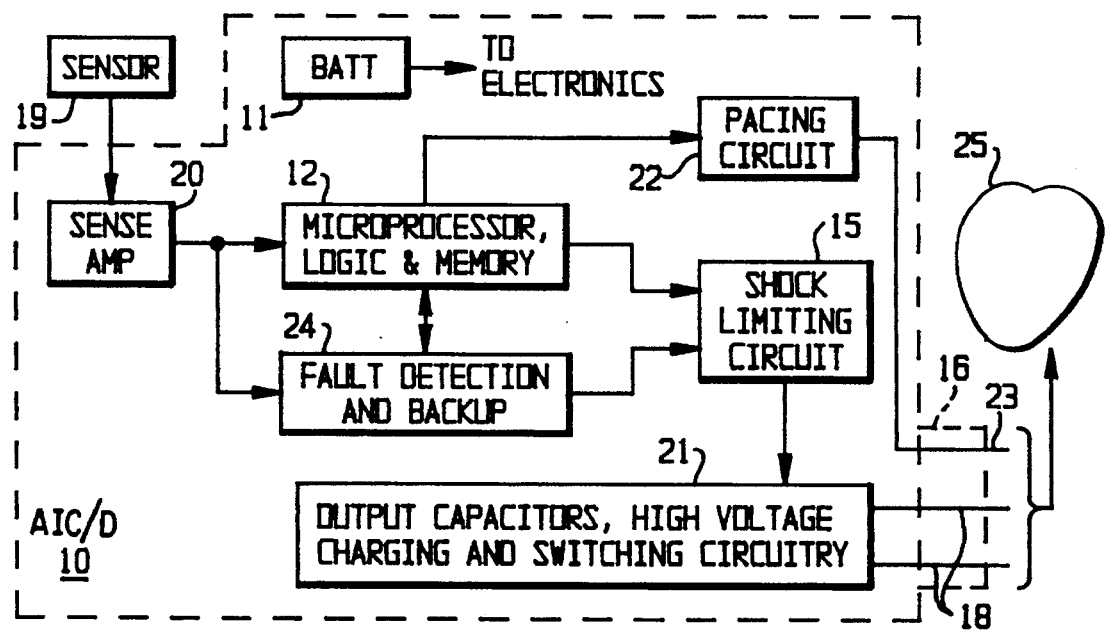
FIG. 1 is a simplified block diagram of an automatic implantable cardioverter/defibrillator which provides multiple functions for treating cardiac rhythm disorders, and which includes backup defibrillation capability.

Referring now to FIG. 1, an ICD 10 is conventional in all respects except for a fault detection and backup system 24 to be described presently. The ICD in this example is adapted to detect and treat various cardiac rhythm disorders by means of bradycardia pacing, antitachycardia pacing, cardioverting and defibrillating therapies, although the principles of the invention may be applied in a device which is restricted to defibrillation alone, if desired. ICD 10 is housed in a conventional hermetically sealed case 17 (often termed a can) composed of biocompatible material for implantation in the body of a patient. The device is powered by a battery pack 11 which may include one or more cells. The device is controlled in principal part by a semiconductor microprocessor 12 with related logic and memory.

Cardioversion and defibrillation therapy of device 10 is provided by an electrical shock waveform delivery system which includes output capacitors together with a high-voltage charging circuit and output switching circuitry, all depicted as being contained in block 21. The output capacitors are adequate to store a level of electrical energy sufficient for defibrillation when delivered via electrodes to the patient's heart in a predetermined high energy single phase or multiphase shock waveform. Shock limiting circuitry 15 is selectively employed to limit the total number of output shocks delivered to the patient's heart. The output circuit of device 10 is connected to an electrical connector 16 mounted to a header on the exterior surface of case 17. Terminals at the proximal end of lead(s) 18 are inserted into receptacles of connector 16 for electrical connection to the circuitry in the case. The distal end of lead 18 is connected to conventional electrodes suitable for cardioverting or defibrillating the patient's heart 25, which may include conventional epicardial patch and/or endocardial electrodes.

Each time a cardioverting or defibrillating shock is to be delivered to the lead for application to the selected chamber of the patient's heart, the high-voltage charging circuit is initiated by the microprocessor to cause the output storage capacitor(s) to be charged to the predetermined energy level. When that level is reached, the capacitors are discharged by the output switching circuit under the control of the microprocessor, to produce the preselected electrical therapy delivery waveform.

For the sake of simplicity, detection of the rhythm disorder(s) to be treated by implanted device 10 is depicted as being performed by a sensor 19, which would typically be part of the electrode system incorporated in the cardiac lead(s). A sense amplifier and related processing circuitry 20 in case 17 receives and processes the electrical signals representative of cardiac activity from sensor 19, for application to the microprocessor. The microprocessor, logic circuitry, associated memory and software operate in part to assess conventional criteria such as ECG morphology, sudden onset, heart rate, rate stability, sustained rate, and so forth, from the processed sense signal, for detecting pathologic tachycardia or fibrillation, and for responding to initiate delivery of appropriate electrical waveform therapy.

Device 10 may be equipped for conventional treatment of bradycardia and tachycardia as well, by a pacing circuit 22 which supplies relatively low energy output pulses for stimulating the heart to a lead 23 (which may be part of lead 18) under the control of the microprocessor and related electronic circuitry 12.

Cardiac activity is monitored by sensor 19 following delivery of the prescribed electrical output waveform to the patient's heart. In the case of antitachycardia, cardioversion or defibrillation, if the sense signal indicates that the therapy was unsuccessful, the same or another waveform is generated according to the prescribed protocol as part of the therapy regimen programmed in the implanted device. The therapy may be programmed for progressively more aggressive treatment with an accelerating tachycardia, in an effort to break the tachycardia before fibrillation possibly occurs. For example, the waveform therapies available from device 10 may include single pacing pulses, pulse sequences, pulse trains of variable repetition frequency, one or more bursts of pulses, and single phase or multiple phase shocks of variable energy content.

The ICD 10 is modified according to the principles of the present invention to provide a backup or standby support system 24 for avoiding catastrophic failure of the implanted device other than complete failure of its power supply. System 24 includes electrical connections to the sense amplifier, microprocessor, and output circuits of the device, but is normally not involved in the operation of the device which has been described.

Figure 2:
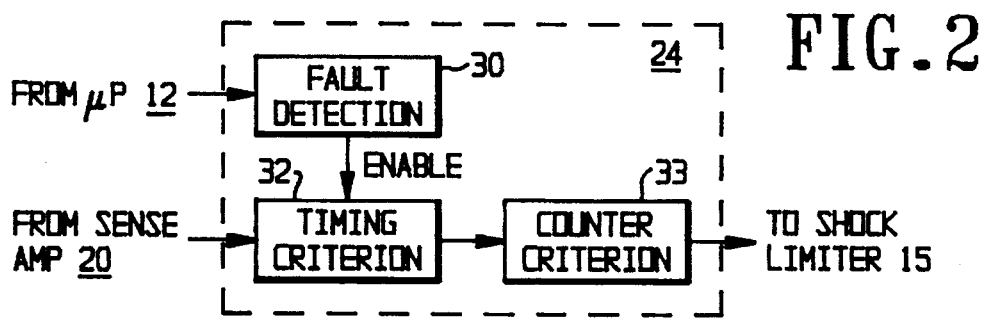
FIG. 2 is a block diagram of an embodiment of a backup portion of the cardioverter/defibrillator to provide a secondary mode of control upon failure of the therapy delivery system of the device.

As shown in FIG. 2, system 24 includes a fault detection circuit 30 electrically coupled to the microprocessor, logic and memory circuitry 12, a timing criterion circuit 32 which receives input signals from both the fault detection circuit and the sense amplifier 20, and a counter criterion circuit 33, connected to receive the output from the timing criterion circuit and to supply an input to the shock limiter 15. In conventional devices, if the primary control mode of the device were shut down, by a failure or malfunction that renders it inoperative, the entire operating system of the implanted device will fail. In those circumstances, the patient is left unprotected from fibrillation.

The secondary control mode system 24 seizes control of the operating system of the device upon failure of the primary control mode. In the preferred embodiment, fault detection circuit 30 detects preselected types of failure mechanisms of the device such as a parity error, the timing out of a watchdog timer, or an inoperative crystal oscillator in the device timing control system, or an inability of the device to access a particular I/O location. If such failure adversely affects the normal operation of the defibrillation portion of device 10, system 24 becomes a redundant system and assumes control to assure that the patient control is not subjected to a life-threatening malfunction. This gives the patient sufficient time to seek medical assistance and to allow device replacement.

In the preferred embodiment, backup system 24 is enabled upon detection of a fault by circuit 30. The enabling signal from the fault detection circuit triggers timing criterion circuit 32 to assess the processed sense signal from sense amplifier 20. Circuit 32 measures the heart rate by application of timing criterion to determine whether the rate is sufficiently high to declare that fibrillation is occurring. If it is not, the timing criterion continues to be applied to the sense amplifier signal. But if the timing criterion is satisfied, the signal is applied to counter criterion circuit 33 to count the number of fibrillation intervals until the number is sufficient to satisfy a sustained fibrillation rate criterion. This assessment is an example only; other suitable criteria may be examined instead, such as X out of Y intervals, to confirm ongoing fibrillation.

If the sustained fibrillation rate criterion is satisfied, the fibrillation therapy delivery portion of ICD 10 is the same as before. Shock limiter circuit 15 keeps track of the total number of shocks which are delivered to the patient's heart in this sequence, and, until the preselected limiting number is reached, activates the high voltage charging circuit to charge the output storage capacitors to the preprogrammed energy level for subsequent discharge to produce the defibrillating shocks. Then, cardiac activity is reassessed to determine whether the therapy was successful. If not, the output storage capacitors are charged again, and the same or a modified defibrillation waveform is generated according to the preprogrammed protocol for this therapy.

Figure 3:
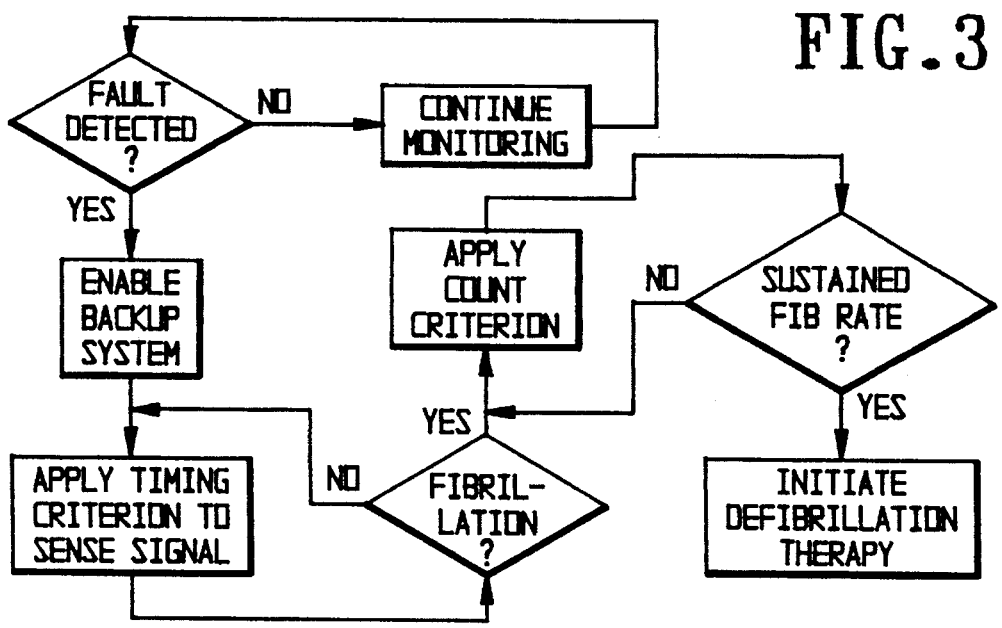
FIG. 3 is a flow diagram of the method of operation of the backup defibrillator.

In the device-implemented method practiced by the preferred embodiment, illustrated in the flow diagram of FIG. 3, backup system monitors the primary mode for faults that could render it inoperative. On detecting such a fault, the backup system is enabled. The timing criterion is then applied to the sense signal to determine whether the rate is high enough to be considered fibrillation. If fibrillation is occurring based on the timing criterion having been satisfied, the number of fibrillation intervals is counted to indicate sustained fibrillation rate. If sustained fibrillation rate is found, defibrillation therapy is initiated.

Although a preferred embodiment and method have been disclosed herein, it will be recognized by those skilled in the art to which the invention pertains from consideration of the foregoing description that variations and modifications of the disclosed embodiment and method may be made without departing from the spirit and scope of the invention. Accordingly, it is intended that the invention shall be limited only as required by the appended claims and the rules and principles of applicable law.

What is claimed is:

1. A cardioverter/defibrillator device structured to be implanted in a patient's body for automatic response to sensing of electrical cardiac activity of the patient's heart to detect and treat disorders thereof, comprising:

primary control mode means responsive to detection of fibrillation of the patient's heart for causing the generation of a prescribed electrical waveform regimen as electrical defibrillation therapy for application to the heart, and secondary control mode means responsive to a predetermined type of failure mechanism of the device that causes malfunction of the primary control mode means for thereupon assuming control of generation of the electrical defibrillation therapy from the primary control mode means, and further responsive to detection of fibrillation after assuming said control to cause the generation of the electrical fibrillation therapy as a backup system for defibrillation of the patient's heart.

2. The device of claim 1, wherein:

the secondary control mode means includes fault detection means for detecting said predetermined type of failure mechanism.

3. The device of claim 2, including:

sensor means for detecting electrical cardiac activity of the patient's heart, and separate detection means for each of said primary and secondary control mode means responsive to said electrical cardiac activity of the patient's heart for detecting fibrillation thereof.

4. The device of claim 3, wherein the sensor means includes:

electrode means for detecting electrical cardiac activity of the patient's heart and transmitting an electrical signal indicative thereof, sense amplifier means operatively coupled to the electrode means for processing the transmitted electrical signal, and operatively coupled to each of the primary control mode means and the secondary control mode means for applying the processed electrical signal thereto.

5. The device of claim 4, wherein the detection means for the primary control mode means includes microprocessor means responsive to the processed electrical signal to detect fibrillation of the patient's heart and initiate said electrical defibrillation therapy.

6. The device of claim 5, wherein the microprocessor means includes means for applying fibrillation detection criteria to the processed electrical signal to detect fibrillation of the patient's heart, wherein said fibrillation detection criteria are selected from a group including fibrillation rate, sustained fibrillation rate, sudden onset, rate stability, and combinations of criteria within said group.

7. The device of claim 4, wherein the detection means for the secondary control mode means includes:

first means responsive to the processed electrical signal for preliminarily detecting fibrillation of the patient's heart after the assumption of control by the secondary control mode means, and confirmation means operatively coupled to the first means and responsive to preliminary detection of fibrillation by said first means for applying preset criteria to the processed electrical signal to confirm ongoing fibrillation of the heart.

8. A method of delivering electrical defibrillation therapy to a patient's heart from an implanted cardiac therapy device after malfunction of the device, comprising the device-implemented steps of:

detecting a predetermined failure mechanism causing malfunction in a primary control mode subsystem of a therapy delivery system of the device, automatically enabling a secondary control mode subsystem of the therapy delivery system as a backup control mode upon detecting said failure mechanism, sensing the patient's cardiac activity to detect fibrillation, and causing generation of a preselected therapy regimen by the enabled secondary control mode subsystem upon confirming sustained fibrillation.

9. The method of claim 8, wherein the steps of sensing and confirming are performed by applying predetermined fibrillation detection criteria to a signal representative of patient cardiac activity.

10. A defibrillator adapted to be implanted in a patient to monitor cardiac activity and to respond to fibrillation of the patient's heart by generating defibrillation therapy, comprising:

means for generating defibrillation therapy, a primary system to initiate said generation of defibrillation therapy for application to the heart, a fault detector for sensing a defect of said primary system that prevents initiating said generation of defibrillation therapy by the primary system; and a standby system responsive to sensing of a defect by said fault detector for replacing the defective primary system, and responsive to heart rate indicative of fibrillation for initiating said generation of defibrillation therapy to be applied to the heart.

11. The defibrillator of claim 10, wherein:

said standby system includes confirmation means responsive to preliminary indication of fibrillation from said heart rate for detecting sustained fibrillation before initiating said generation of defibrillation therapy.

12. The defibrillator of claim 11, wherein:

said fault detector comprises detection circuitry for detecting a fault selected from the group consisting of parity error, timing out of a watchdog timer, a failure in timing control of the primary system, and an inability of the primary system to write to a desired input/output location.

* * * * *